United States Patent [19]

Amer

[11] Patent Number: 4,866,046

[45] Date of Patent: Sep. 12, 1989

[54] LOW-DOSAGE SUBLINGUAL ASPIRIN

[75] Inventor: Moh. S. Amer, Santa Barbara, Calif.

[73] Assignee: Top Laboratories, Inc., Greenwich, Conn.

[21] Appl. No.: 199,679

[22] Filed: May 31, 1988

[51] Int. Cl.$^4$ .............................................. A61U 31/60
[52] U.S. Cl. .................................................... 514/159
[58] Field of Search ................................. 514/159–164

[56] References Cited

U.S. PATENT DOCUMENTS 2,101,867  12/1937  Miller et al. ........................ 514/162
4,579,843   4/1987  Ehrenpreis et al. ................. 514/162

*Primary Examiner*—Stanley J. Friedman
*Attorney, Agent, or Firm*—Samson B. Leavitt; Michael A. Leavitt

[57] ABSTRACT

For better control of pain, fever, inflammation and platelet aggregation in the human blood system, a tablet containing a relatively smaller amount of aspirin capable of rapid dissolution or disintegration in the oral, preferably sublingual, cavity permitting rapid absorption of the aspirin from the saliva into the blood system, and method of using such tablet.

20 Claims, No Drawings

LOW-DOSAGE SUBLINGUAL ASPIRIN

This invention relates to aspirin, and especially to the preparation and use of aspirin in solid form for controlling platelet aggregation in the human blood system.

One of the mechanisms of the action of aspirin that has come to light in recent years is its inhibition of cyclooxygenase. This enzyme converts arachidonic acid to a family of potent local hormones called prostaglandins. By inhibiting cyclooxygenase, aspirin inhibits the production of prostaglandins which are thought to mediate, among other things, pain and inflamation, thus resulting in the anti-inflamatory and analgesic effects of aspirin.

Another activity of the prostaglandins that is strongly affected by aspirin is platelet aggregation. The latter process appears to be regulated via proaggregatory prostaglandins (such as Throboxane) produced by the platelets themselves and antiaggregatory prostaglandins (such as prostacyclin) produced by the arterial cell walls. The state of aggregability of the platelets depends on the balance between these two opposing types of prostaglandins. Large doses of aspirin can inhibit the production of both types with minimal effects on platelet aggregation. Smaller doses of aspirin can preferentially inhibit platelet production of the proaggregatory prostaglandins leaving the arterial wall's antiaggregatory prostaglandins relatively uninhibited. This results in significant platelet aggregation inhibition.

Platelet aggregation is thought to play a major role in the development of myocardial infarctions (heart attacks) and strokes, hence the interest in platelet aggregation inhibition. Aspirin appears to inhibit the cyclooxygenase enzyme through transfer of the acetyl group thus producing an acetylated enzyme which is inactive. In the process, aspirin itself is converted from acetyl salicylic acid to salicylic acid which cannot inactivate the enzyme. Thus, it is the acetyl moiety in the acetylsalicylic acid and not salicylic acid that is active in this system.

The problem with using daily aspirin dosage for the prevention of myocardial infarction and stroke (which is presently advocated by the medical community) is the dose to use. Aspirin is deacetylated in the gastrointestinal tract to a variable but significant extent in different people. Some people are more active deacetylators than others. Thus, the amount of acetylsalicylic acid that escapes deacetylation in the digestive tract and reaches the blood with its acetyl group still attached is very variable. In some people, a dose of 325 mg/day is enough to inhibit platelet aggregation by 90%. In others, doses higher than 2000 mg. may be needed. Still, in some others a dose of only 100 mg. may be all that is needed and 325. mg may be too much, i.e. inhibits the enzyme in both the platelets and arterial walls with no net effect on platelet aggregation.

Another problem with the ingestion of aspirin in tablet and other forms directly into the stomach for the above-described prevention of myocardial infarction and stroke and for other known, e.g. anti-inflammatory, antipyretic, and analgesic, purposes is the ever-present danger of stomach irritation and ulcers probably related to the deacetylation/hydrolysis of the aspirin in the stomach.

U.S. Pat. No. 4,206,209 to Kracauer describes a sublingual aspirin table formulated with specific proportions of specific excipient components and purporting to be practically tasteless, to have a certain porosity, to dissolve rapidly, uniformly and completely under the tongue, to be promptly absorbed without irritation or decomposition into the blood stream, to prevent aspirin decomposition and gastric disturbance in the stomach, to eliminate the necessity of using water or other liquid for swallowing the tablet, and to provide faster relief of pain. This patent fails to recognize or teach the use of aspirin to prevent myocardial infarction and stroke and the necessity of using relatively low dosages of the aspirin for such use. Accordingly no tablet is described containing less than 300 mg. of aspirin.

U.S. Pat. No. 4,539,315 to Bender also describes a sublingual aspirin tablet containing 33.3% to 222% of unreacted glycine by weight of the aspirin and purporting to suppress the normally bitter taste and in vivo breakdown of aspirin in the treatment of pain and chronic arthritis. This patent is similarly deficient with respect to low dosages and prevention of myocardial infarction and stroke, and only describes a tablet containing 325 mg. of aspirin.

An object of this invention is the provision of an aspirin product and its manner of use which will not be subject to the above problems. Another object of this invention is the provision of an aspirin product and its manner of use which substantially avoids the problem of deacetylation in the gastrointestinal tract leading to stomach irritation and ulcers and reducing the proportion of aspirin per se absorbed into the blood system. A further object of this invention is the provision of an aspirin product and its manner of use which eliminates the often troublesome act of swallowing an aspirin tablet, especially with water or other liquid. Still a further object of this invention is the provision of an aspirin product and its manner of use permitting more rapid and efficient inhibition of platelet aggregation and more rapid and efficient inhibition and control of pain, fever, inflammation, rheumatism, arthritis and the like with a dosage considerably smaller than the dosage provided by the usual 325 mg. aspirin tablet.

According to certain aspects of this invention, the attainment of the above objectives is based upon the provision of an aspirin tablet designed to rapidly disintegrate or dissolve in the mouth, preferably the sublingual oral cavity, and the aspirin absorbed into the blood system from the saliva, thus escaping gastrointestinal deacetylation and producing predictable inhibiting effects on platelet aggregation. Such a tablet may contain about 30 to about 190 mg., preferably about 50 to about 145 mg., still more preferably about 70 to about 90 mg., of aspirin, the tablet to be administered orally, preferably sublingually, to the living human as needed or 1 to 7 times a week or preferably on a daily basis and permitted to dissolve in the oral, preferably sublingual, cavity.

Sublingual administration has been found to be highly preferred in promoting more rapid absorption of the aspirin into the blood system due to the relatively large amount of salivary liquid generally present in the sublingual cavity and/or the favorably rapid dissolving or disintegrating property of such salivary liquid on the tablet. Administration to and dissolution in other areas of the oral cavity is also effective though less preferred.

Use of the above-described oral-dissolving low dosage aspirin tablets according to this invention has been found to enable improved control and suppression of myocardial infarction and stroke by more rapid and efficient inhibition of platelet aggregation in the blood being especially effective in reducing the risk of recurrent transient ischemic attacks or stroke in men who have had transient ischemia of the brain due to fibrin platelet emboli, and in reducing the risk of myocardial infarction and subsequent death in patients with unstable angina or a prior infarction. This invention also achieves improved and more rapid analgesic, antipyretic and anti-inflammatory effects, especially in the treatment of headaches, muscular aches and pains, bursitis, sprains, toothaches, sinusitis, menstrual discomfort, minor stiffness, aches and pains of arthritis and rheumatism, sore throat, and fever and discomfort of colds and influenza.

To further promote the desired rapid dissolution and/or disintegration of the tablet in the sublingual cavity, the aspirin (acetylsalicylic acid) should preferably be finely ground (e.g. about 40 mesh), microcrystalline or micronized (e.g. about 80% less than 120 microns) particles and also may be in the form of a soluble complex or salt. The term "aspirin" as employed herein is intended to include any available particulate form and such solubilized forms which alternatively may in fact be produced in situ when the tablet is dissolved or disintegrated in the oral, preferably sublingual, salivary fluid by including the complex-forming or salt-forming material with the free aspirin in the tablet.

Solubilization of the aspirin in vivo can be effected in known manner, for example by using a water soluble alkali metal or alkaline earth metal salt, e.g. with sodium, potassium, lithium, strontium, calcium or magnesium, or an amino acid complex, of the acetylsalicylic acid. Any amino acid may be employed, e.g. acid amino, i.e. monoamino-dicarboxylic, acids such as glutamic acid, basic amino, i.e. diamino-monocarboxylic, acids such as lysine, and especially neutral amino, i.e. monoamino-monocarboxylic, acids such as alanine and especially glycine. The amino acid, or any mixture thereof, may be combined, reacted or complexed with the aspirin prior to formulating in the tablet, or it may be mixed dry with the aspirin in the tablet to exert its solubilizing and taste-neutralizing effect in situ in the saliva, as in fact described in the above-mentioned U.S. Pat. No. 4,539,315 with specific reference to glycine. But whereas the glycine:aspirin weight ratio of 1:3 to 2.22:1 specified in the latter patent are operative herein as applied to glycine and the other amino acids, more efficient, faster and improved solubilization and stabilization effects are obtainable using in the instant tablet amino acid, especially glycine, in ratios to aspirin of about 2.5:1 to about 8:1, preferably about 2.5:1 to about 5:1.

To further improve stability of the aspirin and inhibit decomposition thereof in the saliva, it is preferred that the pH of the aspirin/saliva solution be slightly acidic, e.g. about 4, preferably about 6, to 6.9, by including in the tablet in known manner an effective buffering amount of one or more buffering agents such as mono- and di-sodium phosphates and borates, basic magnesium carbonate and combinations of magnesium and aluminum hydroxide.

Further, it is preferred to include in the tablets of this invention about 3 to about 10% of compressible, soluble starch, about 0.1 to about 10% sweetener such as sugar, saccharin, sodium cyclamate or aspartame, and about 0.001 to about 1% of flavor, e.g. mint or citrus such as lemon or orange.

The tablet of this invention may be of any desired size, shape, weight, consistency or hardness, bearing in mind the primary consideration that it should not be swallowed when introduced in the oral cavity. The rapidly dissolving or disintegrating nature of the instant tablets substantially minimizes the possibility of the aspirin being swallowed before and instead of being absorbed from the oral mucosa or saliva. Also, the larger the tablet the less it is likely to be accidentally swallowed, but the longer it will take to dissolve or disintegrate. Too large a size would be uncomfortable and/or unacceptable to the user. For example, a suitable form of tablet may be a coin-shaped disc or wafer of about 4 to about 15 mm. in diameter and about 5 to 2 mm. in thickness usually varying inversely to the diameter and about 50 to about 1,000 mg. weight. A shape like in ordinary aspirin tablet but half the size would be eminently acceptable. In addition to disc, wafer or coin shapes, the tablet could be in the form of a cube, sphere, cylinder, etc.

In general, the tablet of this invention is typically of homogeneous composition, it being only essential that it dissolves or disintegrates rapidly in the oral, preferably sublingual, cavity to release its aspirin content therein over a period of about 2 seconds or less to about 60 seconds or more, preferably about 3 to about 45 seconds, more preferably about 5 to about 15 seconds. Instead of being homogeneous, the tablet may be composed of layers of aspirin composition separated by non-aspirin layers in repeating or non-repeating sequence.

The tablet of this invention may be made in any known manner and may contain, in addition to the required amount of aspirin, any one or more of the conventional additives or excipients commonly employed in making troches, tablets, lozenges, etc. The tablet may typically contain about 5 to about 60, preferably about 8 to about 40, more preferably about 10 to about 25 wt.% of aspirin, the remainder being the conventional excipients, including fillers, carriers, diluents, bulking or functional agents such as binders, lubricants, disintegrants, and colors such as the following:

As diluents, dicalcium phosphate, calcium sulfate, lactose, cellulose, kaolin, mannitol, sodium chloride, dry starch, powdered sugar, sorbitol, inositol, microcrystalline cellulose, xylitol, sorbitol, hydrogenated starch hydrolysate, hycasin, hydrogenated glucose, hydrogenated di- and poly-saccharides.

As binders, acacia, sodium alginate, extract of Irish moss, gum arabic, panwar gum, ghatti gum, mucilage of isapol husks, carboxymethylcellulose, hydroxyethylcellulose, methylcellulose, polyvinylpyrrolidone, Veegum, larch arabogalactan, gelatin, Kappa carrageenan, copolymers of maleic anhydride with ethylene or vinyl methyl ether.

As lubricants, talc, magnesium stearate, calcium stearate, stearic acid, hydrogenated vegetable oils, carbowax.

As disintegrants, other starches, clays, celluloses, algins, gums, crosslinked polymers (including croscarmelose, crospovidone and sodium starch glycolate), Veegum HV, agar, bentonite, natural sponge, cation exchange resins, aliginic acid, guar gum, citrus pulp, sodium lauryl sulphate.

Natural and/or synthetic colors,

The following examples are only illustrative of the nature of the present invention, and not to be regarded as limiting. All amounts and proportions referred to herein and in the appended claims are by weight unless otherwise indicated.

EXAMPLE 1

|  | Per Tablet | For 10,000 Tablets |
|---|---|---|
| Acetylsalicylic acid | 80.0 mg. | 800 gms. |
| Starch | 420.0 mg. | 4,200 gms. |
| Flavor, sweetener | qs | qs |

Dry the starch to a moisture content of 10%, thoroughly mix with acetylsalicylic acid, flavor and sweetener and compress into slugs. Grind the slugs to 14–16 mesh size and recompress into tablets each weighing about 0.5 gms.

EXAMPLE 2

The following table shows the results of a test with a group of volunteers as averages of the ranges in parantheses.

| Aspirin Daily Dose | % Inhibition, after 5–7 days, of | |
|---|---|---|
|  | Cyclooxygenase | Platelet Aggregation |
| 10 mg. tablet, swallowed | 55.6 (11–95) | 27.5 (0–87) |
| 80 mg. tablet, swallowed | 76.3 (13–100) | 44.2 (5–98) |
| 325 mg tablet, swallowed | 97.7 (25–100) | 70.0 (23–99) |
| 20 mg. sublingual tablet | 83.3 (75–94) | 45.3 (35–60) |
| 80 mg. sublingual tablet | 99.0 (95–100) | 95.7 (88–100) |
| 325 mg.sublingual tablet | 100.0 | 78.5 (62–98) |

Platelet aggregation was measured against thrombin as aggregating agent. Tablets were all similarly made as described in Example 1. The results show higher and more consistent inhibition of enzyme and platelet aggregation in the blood when the aspirin was administered by sublingual tablet according to this invention, especially the tablet of Example 1.

EXAMPLE 3

The following formulation is further illustrative of preferred embodiments of this invention:

|  | Parts | Parts |
|---|---|---|
| Compressible soluble starch | 6.5 | 3–10 |
| Glycine | 65.0 | 50–80 |
| Micronized aspirin | 16.0 | 10–22 |
| Lactose | 5.0 | 2–8 |
| Sugar | 4.5 | 2–7 |
| Dicalcium phosphate | 1.0 | 0.2–3 |
| Gum arabic | 0.5 | 0.2–3 |
| Methyl cellulose | 1.0 | 0.2–3 |
| Guar gum | 0.5 | 0.2–3 |

This formulation is tabletted in conventional manner into tablets of the following specifications:

|  |  | Range |
|---|---|---|
| Appearance: | White biconvex disc |  |
| Average weight: | 259.9 mg. | 255–265 mg. |
| Diameter: | 8.5 mm. | 8–9 mm. |
| Center Thickness: | 4.31 mm. | 4.20–4.40 mm. |
| Disintegration Time: | 10 seconds | 3–45 seconds |
| Friability* | 1.9% | <2.5% |
| Hardness | 36.3 N(Newtons) | 30–60 N |
| Aspirin Content (by titration) | 78.16 mg. | 76–84 mg. |
| Free Salicylic Acid | <0.15% | <2.0% |
| (Colorimetric, relative to aspirin) |  |  |

*Measured on a Roche Friabilator

This invention has been disclosed with respect to preferred embodiments and it will be understood that modifications and variations thereof obvious to those skilled in the art are to included within the spirit and purview of this application and the scope of the appended claims.

What is claimed is:

1. A method of inhibiting platelet aggregation in the blood system of a human who has a need for such inhibition comprising administering to, and letting dissolve in, the oral cavity of said human a tablet which disintegrates in human saliva in less than about 60 seconds containing about 30 to about 190 mg. of aspirin.

2. A method according to claim 1 wherein said tablet contains about 50 to about 145 mg. of aspirin.

3. A method according to claim 1 wherein said tablet contains about 70 to about 90 mg. of aspirin.

4. A method according to claim 3 wherein said tablet further contains glycine.

5. A method according to claim 3 wherein said tablet further contains glycine in a glycine:aspirin weight ratio of about 2.5:1 to about 8:1.

6. A method according to claim 1 wherein said tablet further contains glycine.

7. A method according to claim 1 wherein said tablet further containing glycine in a glycine:aspirin weight ratio of about 2.5:1 to about 8:1.

8. A method according to claim 1 wherein said tablet so disintegrates in about 3 to about 15 seconds.

9. A method according to claim 8 wherein said tablet contains about 70 to about 90 mg. of aspirin.

10. A method according to claim 9 wherein said tablet further contains glycine in a glycine:aspirin weight ratio of about 2.5:1 to about 8:1.

11. A method of inhibiting platelet aggregation in the blood system of a human who has a need for such inhibition comprising administering to, and letting dissolve in, the sublingual oral cavity of said human a tablet which disintegrates in human saliva in less than about 60 seconds containing about 30 to about 190 mg. of aspirin.

12. A method according to claim 11 wherein said tablet contains about 50 to about 145 mg. of aspirin.

13. A method according to claim 11 wherein said tablet contains about 70 to about 90 mg. of aspirin.

14. A method according to claim 13 wherein said tablet further contains glycine.

15. A method according to claim 13 wherein said tablet further contains glycine in a glycine:aspirin weight ratio of about 2.5:1 to about 8:1.

16. A method according to claim 11 wherein said tablet further contains glycine.

17. A method according to claim 11 wherein said tablet further contains glycine in a glycine:aspirin weight ratio of about 2.5:1 to about 8:1.

18. A method according to claim 11 wherein said tablet so disintegrates in about 3 to about 15 seconds.

19. A method according to claim 18 wherein said tablet contains about 70 to about 90 mg. of aspirin.

20. A method according to claim 19 wherein said tablet further contains glycine in a glycine:aspirin weight ratio of about 2.5:1 to about 8:1.

* * * * *